United States Patent [19]
Thornton

[11] Patent Number: 5,566,692
[45] Date of Patent: Oct. 22, 1996

[54] DENTAL FLOSS PACKAGE

[76] Inventor: Thomas E. Thornton, 43 Contentment Island Rd., Darien, Conn. 06820

[21] Appl. No.: 235,703

[22] Filed: Apr. 29, 1994

[51] Int. Cl.⁶ ..................................... A61L 15/00
[52] U.S. Cl. .......................... 132/324; 132/329; 206/63.5; 206/388
[58] Field of Search ................... 132/323, 324, 132/321, 329; 206/388, 63.5, 494, 233

[56] References Cited

U.S. PATENT DOCUMENTS

| | | | |
|---|---|---|---|
| 4,574,952 | 3/1986 | Masui | 206/494 |
| 4,972,946 | 11/1990 | Whittaker | 132/324 |
| 5,024,324 | 6/1991 | Whittaker | 132/324 |
| 5,074,100 | 12/1991 | Lepie | 132/323 |
| 5,322,077 | 6/1994 | Corella | 132/323 |

Primary Examiner—John G. Weiss
Attorney, Agent, or Firm—James J. McKeever

[57] ABSTRACT

The present invention relates to a package for dispensing cut brushed dental floss and more particularly the present invention relates to a dispensing package for cut brushed dental floss that allows the removal of a single floss one at a time. The novel dispensing package of the present invention consists of an internal control card with an apex fold line and a rear portion on the opposite side of the apex. The cut brushed floss is placed on the control card in a manner where the floss section of the cut brushed floss is in a zigzag folded position on the interior of the control card, the brushed section is on the face portion of the control card and the threader section is led over the apex to the rear portion which holds the brushed section on the face of the card. The package having the loaded card inside has an opening to permit removal of a single cut brushed floss therefrom, one at a time.

2 Claims, 2 Drawing Sheets

DENTAL FLOSS PACKAGE

FIELD OF THE INVENTION

The present invention is related to the field of brushed dental floss and the problem involved in the packaging and dispensing thereof.

BACKGROUND OF THE INVENTION

The present invention was developed because of the need for a dispensing package for brushed dental floss, such as those disclosed in my U.S. Pat. Nos. 3,837,351 issued Sep. 24, 1974 and 4,142,538 issued Mar. 6, 1979. While this type of dental floss has revolutionized the dental floss industry, it has brought with it a packaging and dispensing problem.

The older regular dental floss that comes in a small hard plastic container with a long continuous length strand of 100 to 200 mm and a small cutting edge at the exit window which allows the user to cut a desired length presents no tangling problem. However, with the new brushed dental floss, which is packaged in individual strands consisting of a threader on one end and a flexible floss on the other end with the brushed section in between there exists a problem.

This problem involves the removal of a single strand for use and not pulling out a half dozen or so strands that are co-mingled with the one strand that is desired.

This state-of-the-art dental floss has been on the market for about ten years as has the problem of numerous entangled strands of floss being pulled from a package when a user wishes to extract a single therefrom. The present invention overcomes the inherent dispensing problem of brushed dental floss because it allows the removal of a single strand of brushed dental floss in a one-at-a-time fashion and does not cause the entanglement of the floss remaining in the dispensing package. All of this allows the floss to be pulled out by the brush section which is positioned in the window and not floss section.

SUMMERY OF THE INVENTION

The present invention is unique dispensing package for brushed dental floss which overcomes the main problem encountered with the dispensation of brushed dental floss, namely, ease of removal, elimination of tangling and maintaining a sterile environment for the remaining floss strands. This ease of dispensation is accomplished by providing an innovative control card insert, the innovative method of folding the brushed floss on said control card and the method of placing said floss on said card into the package.

It is important to remember that placing the brushed section of the floss strand in the package window is essential to the present invention since the floss must be pulled out of the package by the rear end of the brush and not the front end. Pulling out by the front end will cause a stretching of the brush section and diminish its effectiveness in removing plaque.

The need for the control card insert is to allow the required folding of the floss section of the brushed floss strand and further allows the brushed section to be positioned to appear in the dispensing window when inserted into the package. The threader section is then lead over the apex of said control card.

By the use of the folded control card and the zig zag method of folding the floss section, placing the brushed section on the face of said folded control card so that it will appear in the package window for dispensing.

The present invention has essentially eliminated the major problem involved in the dispensing of brushed dental floss and at the same time it keeps the remaining brushed floss sterile without loss.

OBJECTS OF THE INVENTION

The object of the present invention is to provide a dispensing package for brushed dental floss that allows the removal of a single strand, one at a time.

Another object of the present invention is to provide a dispensing package for brushed dental floss that prevents tangling of said floss upon removal.

A further object of the present invention is to maintain a sterile environment for those floss that remain in the package.

A still further object of the present invention is to eliminate the loss and contamination enchanted when multiple numbers of stands are removed in an attempt to remove a single strand from a package.

Various other objects, advantages and features of the present invention will become apparent to those skill in the art from the previous and the following discussions, taken in conduction with the accompanying drawings, which constitute a part hereof.

DESCRIPTION OF THE PREFERRED EMBODIMENT OF THE PRISONER INVENTION

Figure 1:
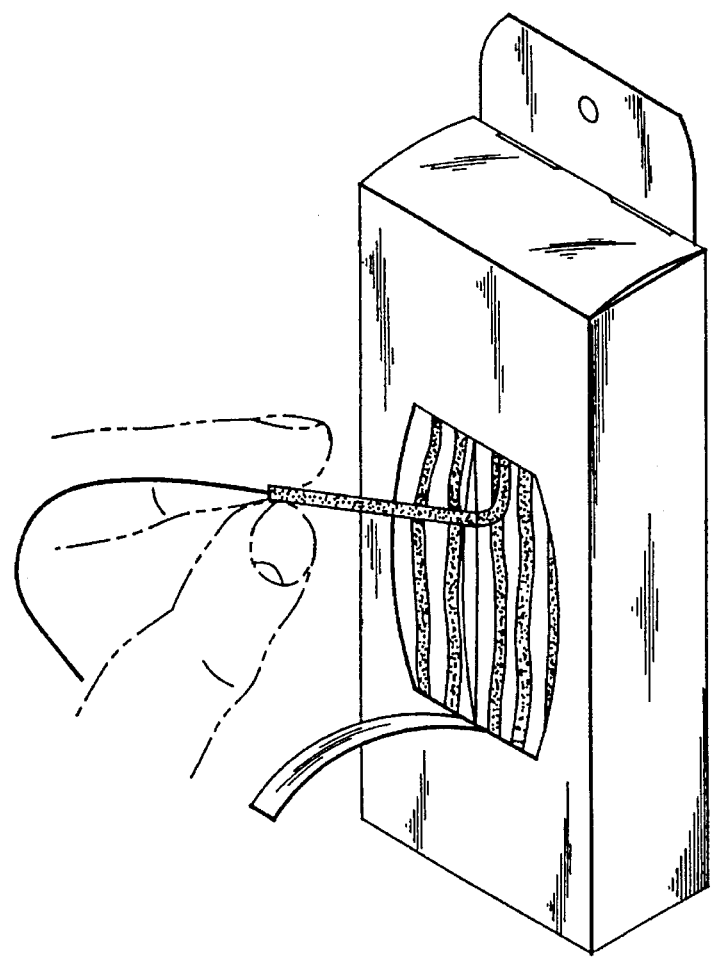
FIG. 1. is a perspective view of the dispensing package of the present invention showing a single strand of brushed floss being removed from said package.

The dispensing package of the present invention is shown in FIG. 1. at 1, the brushed floss is being removed from split 2 in flexible plastic window 3, which appears when tear-away cardboard strip is removed.

Figure 2:
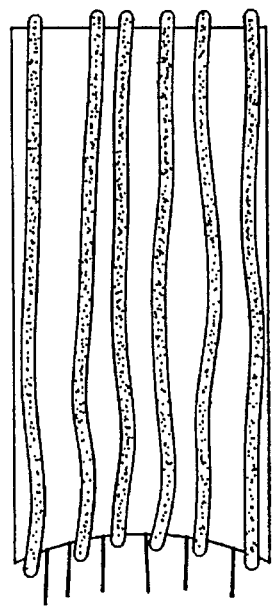
FIG. 2. is a plan view of the foldable control card showing the floss section in the innovative "zig-zag" position on said control card.

The unfolded foldable control card 5 is shown FIG. 2 having the "zig zag" folded floss section at 6 and the card is foldable at 7.

Figure 3:
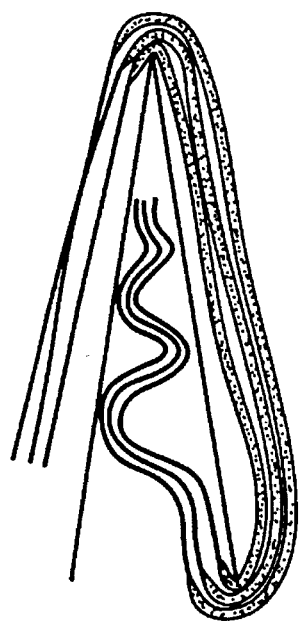
FIG. 3. is aside view of the foldable control card showing the position of the floss section, the brush section and the threader section within the folded control card.

In FIG. 3. the side of control card is at 5, with its apex at 8, the "zig zagged" folded floss section is at 6, the brushed section is at 9 and the threader section is at 10.

Figure 4:
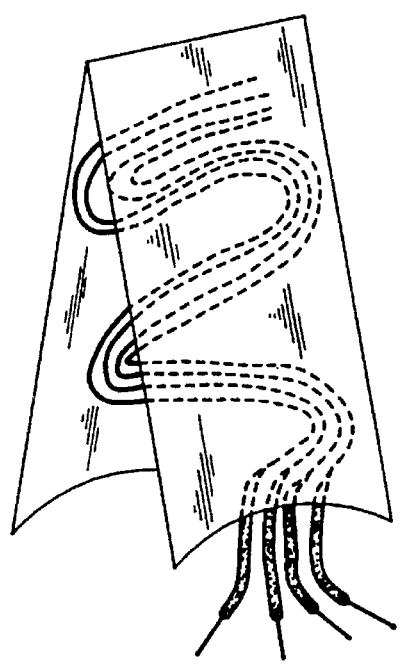
FIG. 4. is a perspective see-through view of the folded control card with the folded control card with the brushed floss positioned therein.

In FIG. 4 the folded control card is shown at 5, the dotted lines illustrate the "zig zagged" floss portion 6' and the brushed section 9 is on the front face 12 of folded control card 5, the threader section 10 is shown going over the apex 8 of said control card.

The loaded control card 5 is shown in FIGS. 3 and 4 and then inserted into dispenser package 1 from the bottom 11 up so that said brushed portion will appear in window 3 while tear-off cardboard strip 4 is covering split 2.

While the above description contains many specificities, the reader would not construe these as limitations on the scope of the invention, but merely as exemplification of a preferred embodiment. Those skilled in the art will envision that many other possible variations are within the scope of the present invention. For example, skilled artisans will readily be able to change the dimensions and the materials of various embodiments. They can make variations on the design of the present invention. Accordingly, the reader is requested to determine the scope of the present invention by the scope of the appended claims and their legal equivalence and not by the examples that have been given.

What is claimed is:

1. A dispensing dental floss package comprising in combination:

a control card having an apex along a fold line, said control card having a face portion on one side of said apex and a rear portion on the opposite side of said apex, said control card defining an interior space between said face portion, rear portion and below said apex, dental floss placed on said control card, said dental floss having a floss section, brush section and threader section, said floss section placed in a zigzag folded position in the interior of said control card, said brush section placed on the face portion of said control card with the threader section extending over said apex to hold said brush section on the face portion of said control card and, a package enclosing said control card, said package having an opening to permit the pulling of said brush section of the dental floss from the control card by a user for flossing.

2. The dispensing package of claim 1 wherein said brush section appears in a window of said package, said window provided with an openable slit and a tear-away cover.

* * * * *